(12) United States Patent
Ferek-Petric

(10) Patent No.: US 7,780,607 B2
(45) Date of Patent: Aug. 24, 2010

(54) CARDIAC THERAPY SYSTEM INCLUDING A TRIBOELECTRIC SENSOR

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 1046 days.

(21) Appl. No.: 11/323,026

(22) Filed: Dec. 30, 2005

(65) Prior Publication Data

US 2007/0156053 A1 Jul. 5, 2007

(51) Int. Cl.
*A61N 1/37* (2006.01)

(52) U.S. Cl. ....................................... 600/508

(58) Field of Classification Search ............... 600/527; 607/115–119
See application file for complete search history.

(56) References Cited

U.S. PATENT DOCUMENTS

| | | | |
|---|---|---|---|
| 2,787,784 A * | 4/1957 | Meryman et al. | 340/596 |
| 4,600,017 A * | 7/1986 | Schroeppel | 607/122 |
| 5,174,303 A | 12/1992 | Schroeppel | |
| 5,261,418 A * | 11/1993 | Ferek-Petric | 607/126 |
| 5,514,171 A * | 5/1996 | Hoegnelid et al. | 607/122 |
| 5,628,777 A * | 5/1997 | Moberg et al. | 607/122 |
| 5,693,074 A * | 12/1997 | Ferek-Petric | 607/9 |
| 6,418,332 B1 | 7/2002 | Mastrototaro et al. | |
| 6,591,143 B1 * | 7/2003 | Ekwall | 607/116 |
| 7,493,164 B1 * | 2/2009 | Koh | 607/23 |

FOREIGN PATENT DOCUMENTS

| | | |
|---|---|---|
| EP | 0473070 A2 | 8/1991 |
| EP | 0632992 A1 | 6/1994 |
| WO | 9515784 | 6/1995 |
| WO | WO9926693 | 6/1999 |

* cited by examiner

*Primary Examiner*—Scott M Getzow
*Assistant Examiner*—Amanda Patton
(74) *Attorney, Agent, or Firm*—Stephen W. Bauer

(57) ABSTRACT

Mechanical activity of a heart is sensed by a cardiac lead that carries a triboelectric sensor. The triboelectric sensor produces a triboelectric signal in response to cardiac contractions. A lead fabricated according to the invention can be used for a variety of purposes, including without limitation, pacing capture verification, electromechanical conductivity status of the myocardium (including detecting relatively reduced myocardial activity indicative of ischemia, myocyte necrosis, arterial stenosis and the like). The sensor allows detection of mechanical activity without signal blanking traditionally utilized to stimulate and sense cardiac activity. Traditional circuitry can be employed to stimulate/sense while a triboelectric sensor unit(s) detect evoked and/or intrinsic mechanical cardiac activity. A reduction from a prior amplitude signal can be used to set patient (or clinician) alert signals, set a logical flag regarding possible lead dislodgement, compare prior and current signals, store same in memory, and/or provide via telemetry for display.

5 Claims, 3 Drawing Sheets

CARDIAC THERAPY SYSTEM INCLUDING A TRIBOELECTRIC SENSOR

BACKGROUND OF THE INVENTION

The present invention relates to cardiac therapy systems. In particular, the present invention relates to a system including a triboelectric sensor for sensing signals related to cardiac contractions.

Implantable medical devices (IMDs) such as cardiac pacemakers, cardioverter defibrillators, and neurostimulators deliver electrical signals to a portion of the body and/or sense electrical signals from the body. A pacemaker includes a pulse generator and one or more leads for delivering generated stimulation pulses to the heart and for sensing cardiac signals and delivering sensed signals from the heart back to the pacemaker. Electrodes on the lead are electrically coupled to an inner lead conductor, which carries the stimulating current or sensed cardiac signals between the electrodes and the implanted device.

The inner lead conductor of the cardiac lead defines a channel within the cardiac lead. This channel enables control of lead implantation with a stylet. After proper positioning of the lead tip, the stylet is pulled out of the stylet channel. As a result, the implanted cardiac lead has an empty stylet channel.

BRIEF SUMMARY OF THE INVENTION

The present invention senses mechanical activity of a heart. A cardiac lead carries a triboelectric sensor that produces a triboelectric signal in response to cardiac contractions. A lead fabricated according to the invention can be used for a variety of purposes, including without limitation, pacing capture verification, electromechanical conductivity status of the myocardium (including detecting relatively reduced myocardial activity indicative of ischemia, myocyte necrosis, arterial stenosis and the like). Such a lead allows detection of mechanical activity without signal blanking oftentimes used with electrodes traditionally utilized to stimulation and sense cardiac activity. Thus, in one form of the invention traditional circuitry and components are employed to stimulate and sense while one or more triboelectric sensor units are employed to detect evoked and intrinsic mechanical cardiac activity. In another form of the invention a reduction from a prior amplitude signal is utilized to provide a patient (or clinician) alert signal, a logical flag is set regarding possible lead dislodgement, a compare prior and current signals, stored same to memory, and/or provide the results via telemetry for remote display and processing and the like.

DETAILED DESCRIPTION

Figure 1:
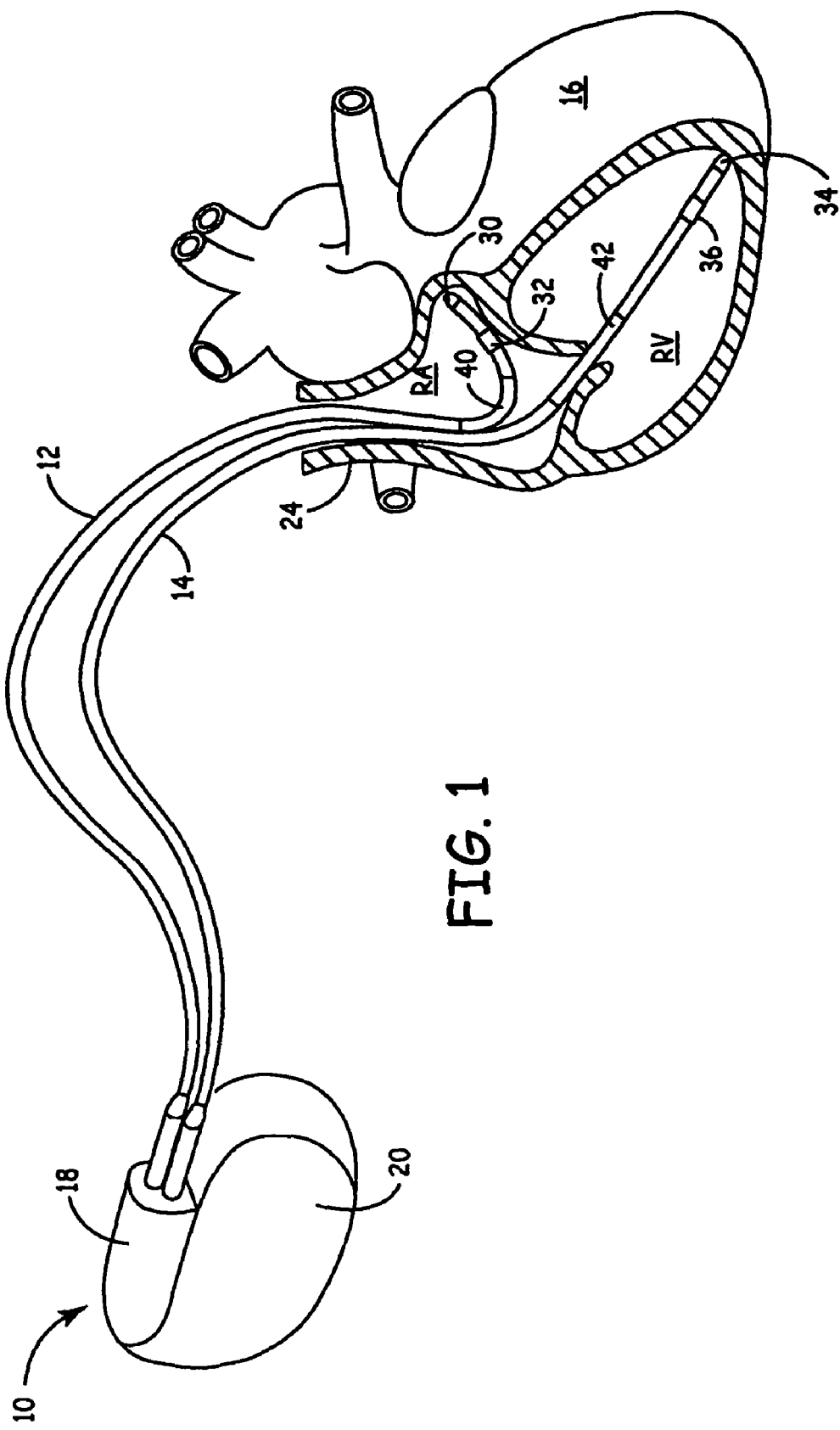
FIG. 1 is a schematic view of an implantable medical device including atrial and ventricular leads.

FIG. 1 is a schematic view of implantable medical device (IMD) 10 including atrial lead 12 and ventricular lead 14 implanted in heart 16. IMD 10 may be a pacemaker, defibrillator, cardioverter, pacemaker/cardioverter/defibrillator (PCD), heart function monitor having pacing capabilities, or other implantable device that includes the capability of providing therapy to heart 16. IMD 10 includes connector module or header 18 and housing 20. Atrial lead 12 and ventricular lead 14 extend from connector module 18 into the right atrium RA and right ventricle RV, respectively, of heart 16. Proximal ends of atrial lead 12 and ventricular lead 14 are connected at header 18 to sensing, signal processing, and therapy delivery circuitry (not shown) within housing 20.

Atrial lead 12 and ventricular lead 14 enter right atrium RA through superior vena cava 24. Atrial lead 12 is a J-shaped bipolar lead including tip electrode 30 and ring electrode 32 at its distal end, while ventricular lead 14 is an elongated bipolar lead including tip electrode 34 and ring electrode 36 at its distal end. While bipolar leads 12 and 14 are disclosed, unipolar leads can alternatively be implanted in the same anatomic relation to the heart chambers.

When heart 16 contracts, atrial lead 12 and ventricular lead 14 are deflected. The atrial contraction causes bending or deformation of atrial lead 12 along bending portion 40, while the ventricular contraction causes bending or deformation of ventricular lead 14 along bending portion 42. The magnitude of the deflection along bending portions 40 and 42 depends on the radial stiffness of atrial lead 12 and ventricular lead 14, respectively, and on the muscle contraction forces of heart 16. In addition, the magnitude of the deflection depends on the initial bending forces caused by the specific implantation position. For instance, atrial lead 12 implanted on the anterior atrial wall (as shown in FIG. 1) has a larger J-shape radius than a lead implanted in the atrial appendage. Atrial lead 12 and ventricular lead 14 are strongly mechanically coupled to the heart muscle, especially in the chronic phase of cardiac pacing when fibrotic tissue anchors the lead tips to the endocardium.

The various types of cardiac rhythms have differing hemodynamics (i.e., different magnitudes and frequency spectra of contraction movements). For example, ventricular tachycardia impedes cardiac contractions significantly, causing a decrease in the contraction magnitude. The different cardiac rhythms cause forces that result in different mechanical tension in atrial lead 12 and ventricular lead 14.

The stylet channel formed by the inner lead conductor of the cardiac lead enables control of lead implantation with a steel wire (i.e., stylet). After positioning of the lead tip, the stylet is pulled out of the stylet channel. As a result, the implanted cardiac lead has an empty stylet channel. The stylet channel may thus be used for permanent insertion of a stylet having sensing capabilities. The present invention is directed to sensing a triboelectric signal produced by surface contact (friction) effects between an inner conductor of the lead and an insulator on a lead stylet.

Figure 2:
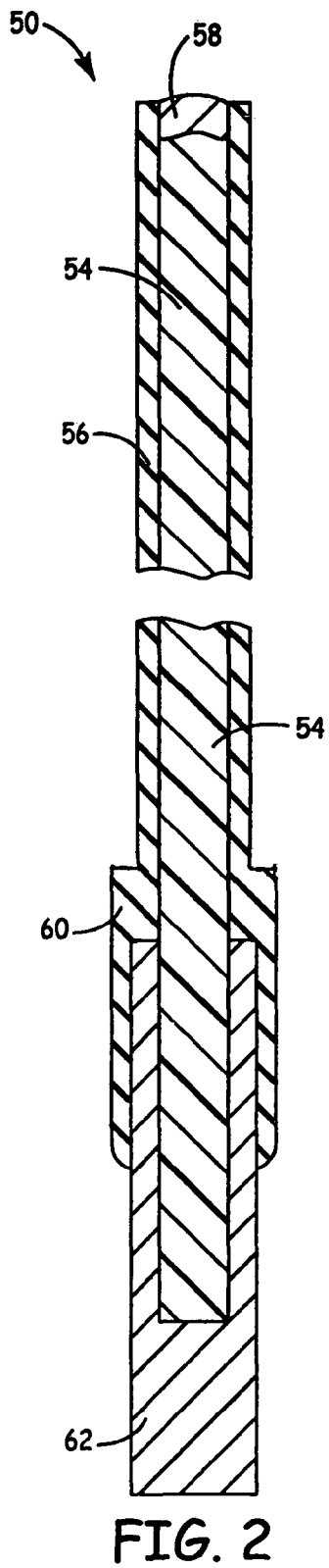
FIG. 2 is a cross-section view of proximal and distal ends of a lead stylet for insertion into a cardiac lead.

FIG. 2 is a cross-section view of proximal and distal ends of lead stylet 50 for insertion into atrial lead 12 or ventricular lead 14. At the distal end, lead stylet 50 includes stylet conductor 54, insulating sheath 56, and stopper 58. At the proximal end, lead stylet 50 includes stylet conductor 54, insulating sheath 56 (which terminates at the proximal end of stylet 50 with insulating connector seal 60), and connector pin 62.

Insulating sheath 56, which is made of a flexible polymeric material, has a diameter such that its exterior surface is coupled to the inner lead conductor that forms the stylet channel in atrial lead 12 or ventricular lead 14 (see FIG. 3). The tip of lead stylet 50 is closed by stopper 58, which may be made of silicone.

When lead stylet 50 is inserted within atrial lead 12 or ventricular lead 14 through the stylet channel formed by the inner lead conductor, the outer surface of insulating sheath 56 mechanically couples with the inner surface of the inner lead conductor. The length of lead stylet 50 is such that a portion of lead stylet 50 is positioned within bending portion of the lead (e.g., bending portion 40 of atrial lead 12 or bending portion 42 of ventricular lead 14). It should be noted that the configuration of lead stylet 50 shown in FIG. 2 is merely illustrative, and any lead stylet including an insulating material surrounding a conductive portion may be employed in accordance with the present invention.

Figure 3A:
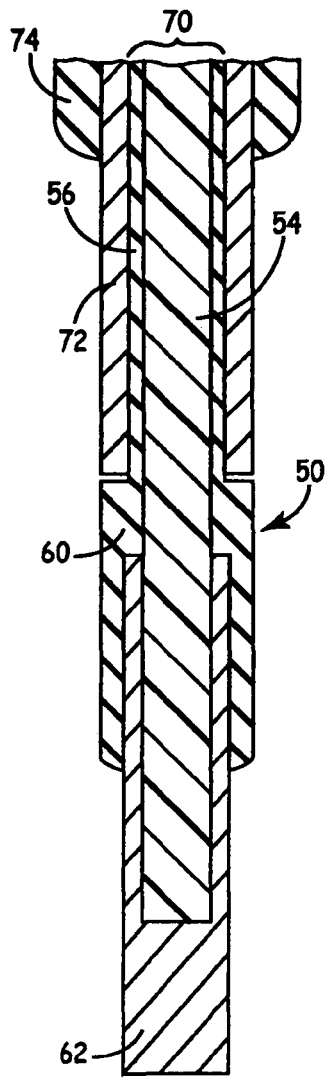
FIG. 3A is a cross-sectional view of a proximal end of a cardiac lead having the proximal end of the lead stylet shown in FIG. 2 inserted therein.
Figure 3B:
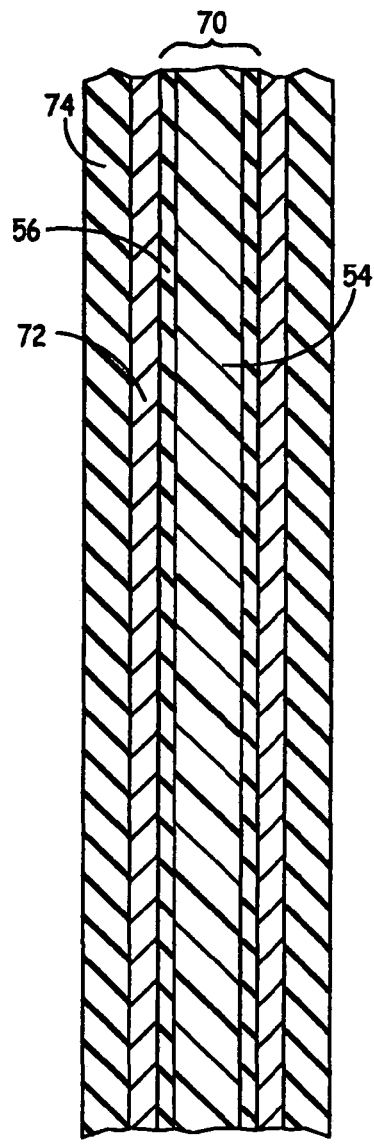
FIG. 3B is a cross-sectional view of a portion of the cardiac lead and lead stylet at a location subject to mechanical stresses due to cardiac contractions.

FIG. 3A is a cross-sectional view of a proximal end of a cardiac lead (e.g., atrial lead 12, ventricular lead 14) including stylet channel 70 defined by inner lead conductor 72 having lead stylet 50 inserted therein. FIG. 3B is a cross-sectional view of the cardiac lead shown in FIG. 3A along a portion of the cardiac lead subject to mechanical stresses due to cardiac contractions (e.g., bending portion 40 on atrial lead 12, bending portion 42 on ventricular lead 14). Stylet 50 is inserted within stylet channel 70, which is defined by inner lead conductor 72 of the cardiac lead. Stylet conductor 54 is terminated at the proximal end of lead stylet 50 with connector pin 62. Connector pin 62 is isolated from inner lead conductor 72 by insulation seal 60. Connector pin 62 and the proximal end of inner lead conductor 72 provide an interface for electrically connecting stylet conductor 54 and inner lead conductor 72 with circuitry within IMD 10.

When lead stylet 50 is subjected to mechanical stresses due to cardiac contractions, an electrical charge differential is generated between insulating sheath 56 and both stylet conductor 54 and lead conductor 72 due to the triboelectric effect. The triboelectric effect is a type of contact electrification in which certain materials become electrically charged after coming into contact with a different material, e.g., by frictional contact. This may occur when lead stylet 50 is subjected to mechanical stresses, such as shock or bending forces. The polarity and strength of the charges generated on the materials differ according to the materials, surface roughness, temperature, strain, and other properties. After coming into contact, a chemical bond is formed between some parts of the contacting surfaces. When the chemical bond is formed between the materials, charges move from one material to the other to equalize their electrochemical potential. This creates a net charge imbalance between the materials. When separated, some of the bonded atoms have a tendency to keep extra electrons, and some have a tendency to give them away.

The triboelectric series is a list of materials, provided in order from materials that have a greater tendency to attain a positive charge after separation, to those that have a greater tendency to attain a negative charge after separation. Thus, a material towards the negative end of the triboelectric series, when touched to a material closer to the positive end of the series, will attain a more negative charge, and vice versa. The further away two materials are from each other on the series, the greater the charge transferred.

Insulating sheath 56 of lead stylet 50 is made of a material that is far on the triboelectric series from the conductive materials that comprise stylet conductor 54 and inner lead conductor 72. In one embodiment, insulating sheath 56 is made of a material toward the negative end of the triboelectric series (e.g., silicone, polyurethane), while stylet conductor 54 and inner lead conductor 72 are made of a conductive material closer to the positive end of the triboelectric series (e.g., platinum, aluminum, steel). Thus, when cardiac contractions bend the portion of lead stylet 50 that is disposed in the bending portion of the cardiac lead (e.g., bending portion 40 of atrial lead 12, bending portion 42 of ventricular lead 14), a negative electrical charge is accumulated in insulating sheath 56 due to the triboelectric effect. The amount of charge that is accumulated in insulating sheath 56 is proportional to the bending angle of the cardiac lead and lead stylet 50 disposed therein. The charge in insulating sheath 56 modulates at a frequency related to the rate of cardiac contractions. Thus, the triboelectric signal occurs at a low frequency (e.g., less than 50 Hz), which is around the frequency of cardiac mechanical activity.

The electrical charges that accumulate on insulating sheath 56 can be measured with a charge or voltage amplifier connected to stylet conductor 54 and inner lead conductor 72. The charge or voltage amplifier may be implemented in IMD 10. Connector pin 76 and the portion of inner lead conductor 72 at the proximal end of lead stylet 50 (which functions as a connector pin for inner lead conductor 72) provide interfaces for electrically connecting stylet conductor 54 and inner lead conductor 72, respectively, to connector module 18 of IMD 10. The output of the charge amplifier is connected to signal processing circuitry in IMD 10, which produces a signal related to cardiac contractions from the measured charge variation.

Figure 4:
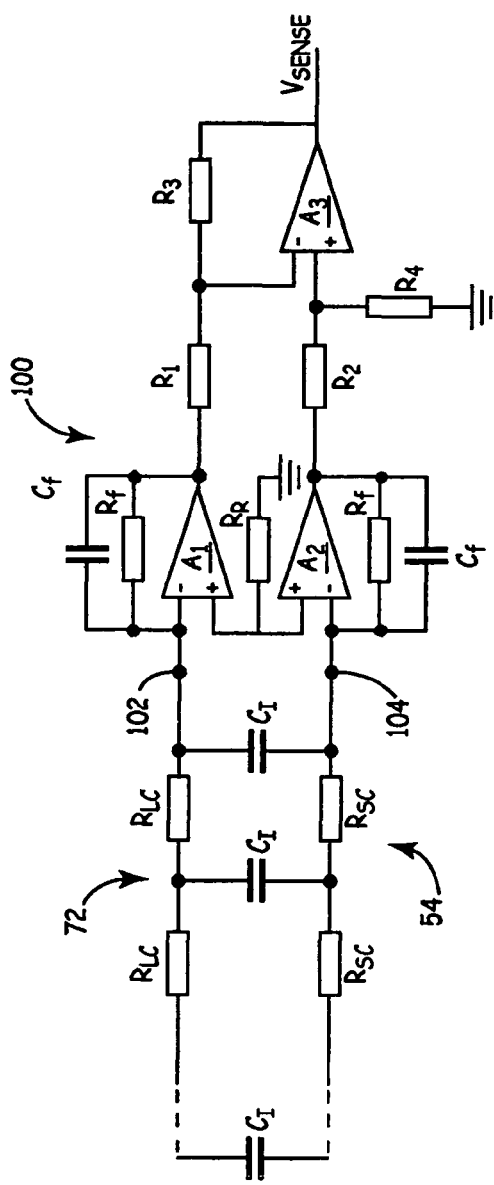
FIG. 4 is a schematic view of an equivalent circuit of a charge differential amplifier connected to an inner conductor of the cardiac lead and a lead stylet conductor.

FIG. 4 is a schematic view of an equivalent circuit for charge differential amplifier 100 with inner lead conductor 72 and stylet conductor 54 connected to inputs 102 and 104, respectively, of charge differential amplifier 100. The distributed capacitance of insulating sheath 56 is represented by capacitors $C_I$, the distributed resistance of inner lead conductor 72 is represented by resistors $R_{LC}$, and the distributed resistance of stylet conductor 54 is represented by resistors $R_{SC}$. It should be noted that while charge differential amplifier 100 is shown and described with regard to FIG. 4, any device capable of measuring signals from lead stylet 50 due to the triboelectric effect may alternatively be connected to stylet conductor 54 and inner lead conductor 72 (e.g., a voltage differential amplifier).

Charge differential amplifier 100 includes operational amplifiers $A_1$, $A_2$, and $A_3$, feedback resistors $R_f$, feedback capacitors $C_f$, reference resistor $R_R$, and resistors $R_1$-$R_4$. Lead conductor 72 is connected to the inverting input of operational amplifier $A_1$, and stylet conductor 54 is connected to the inverting input of operational amplifier $A_2$. Feedback resistors $R_f$ and feedback capacitors $C_f$ are connected between the inverting input and the output of amplifiers $A_1$ and $A_2$. Reference resistor $R_R$ connects the non-inverting inputs of operational amplifiers $A_1$ and $A_2$ to ground. The outputs of operational amplifiers $A_1$ and $A_2$ are connected via resistors $R_1$ and $R_2$ to the inverting and non-inverting inputs, respectively, of operational amplifier $A_3$. Resistor $R_3$ is connected between the non-inverting input of operational amplifier $A_3$ and ground, and resistor $R_4$ is connected between the inverting input and the output of operational amplifier $A_3$.

Operational amplifier $A_1$, feedback resistor $R_f$, feedback capacitor $C_f$, and reference resistor $R_R$ function as a low-pass filter for the signal from lead conductor 72. Operational amplifier $A_2$, feedback resistor $R_f$, feedback capacitor $C_f$, and reference resistor $R_R$ function as a low-pass filter for the signal from stylet conductor 54. The time constant for each of the low-pass filters is $R_f C_f$. As described above, the triboelectric signal occurs at a low frequency (i.e., <50 Hz). Thus, the time constant is selected such that only the signal related to the triboelectric effect is provided at the outputs of operational amplifiers $A_1$ and $A_2$.

Operational amplifier $A_3$ and resistors $R_1$-$R_4$ function as a differential amplifier for the signals provided from operational amplifiers $A_1$ and $A_2$. The differential amplifier provides an output signal $V_{SENSE}$ as a function of the difference between the non-inverting input signal and the inverting input signal to operational amplifier $A_3$. This difference is amplified by a factor determined by the ratio of resistor $R_4$ to resistor $R_1$. The $V_{SENSE}$ signal provided at the output of operational amplifier $A_3$ is related to the varying charge that accumulates in insulating sheath 56 as lead stylet 50 is subjected to mechanical stresses due to cardiac contractions.

Figure 5:
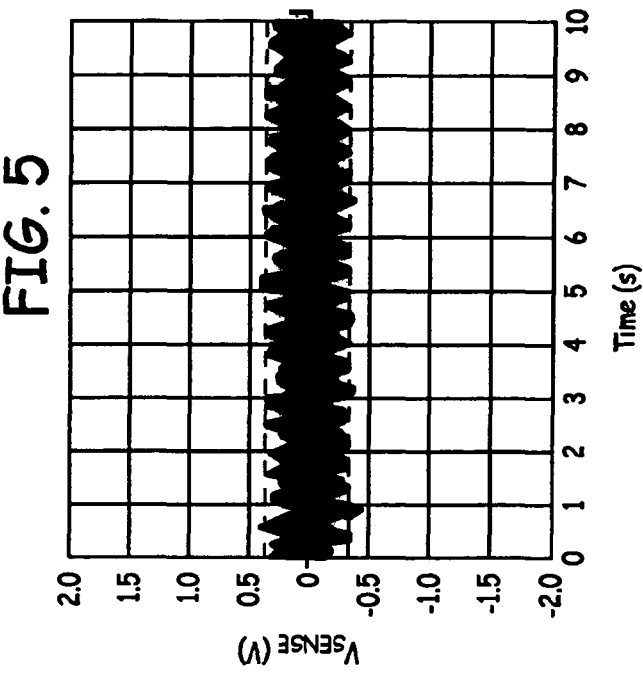
FIG. 5 is a graph showing the output signal of the charge differential amplifier shown in FIG. 4.

FIG. 5 is a graph showing signal at output $V_{SENSE}$ of charge differential amplifier 100 for lead stylet 50 disposed in a cardiac lead. In the tested device, insulation sheath 56 was made of silicone, and stylet conductor 54 and lead conductor 72 was made of a conductive material such as platinum, silver, or steel. Lead stylet 50 was positioned in the cardiac lead so as to enable pendulum movements with an excursion amplitude (i.e., the distance moved by the distal end of the cardiac lead during a cardiac cycle) of about 10 cm. Charge differential amplifier 100 included feedback capacitors $C_f$ having a capacitance of 100 pF and feedback resistors $R_f$ having a resistance of 1 G$\Omega$. The graph shows that the output signal $V_{SENSE}$ was a sinusoidal signal having a peak-to-peak amplitude of about 0.7 V. This translates to a charge variation in insulation sheath 56 of around 70 pC.

The output signal $V_{SENSE}$ may be used by IMD 10 to detect and monitor cardiac contractions in heart 16. This information may be used by IMD 10 to determine frequency, amplitude, and velocity characteristics of the contractions. In addition, the $V_{SENSE}$ signal may be provided to signal processing circuitry in IMD 10 to derive data related to other cardiac parameters, such as contraction parameters for arrhythmia detection, or to produce information for heart failure monitoring. The processed information may be used by IMD 10 to control the therapy delivered by cardiac leads 12 and 14.

In summary, the present invention senses mechanical activity of a heart. A cardiac lead carries a triboelectric sensor that produces a triboelectric signal in response to cardiac contractions. In one embodiment, triboelectric sensor includes an inner lead conductor that defines a stylet channel and a stylet that includes a stylet conductor within an insulating sheath. At least a portion of the stylet is disposed in the stylet channel at a sensing location. A charge amplifier is connected to the inner lead conductor and the stylet conductor for producing an output signal based upon a triboelectric charge on the insulating sheath caused by movement of the lead due to the cardiac contractions. The output signal of the charge amplifier may be processed to produce information related to cardiac activity that may be used in cardiac diagnosis and therapy.

Although the present invention has been described with reference to preferred embodiments, workers skilled in the art will recognize that changes may be made in form and detail without departing from the spirit and scope of the invention.

The invention claimed is:

1. A method for sensing mechanical activity of a heart, the method comprising:
    disposing a sensor at a location in the heart to subject the sensor to mechanical stress due to cardiac contractions; and
    measuring a triboelectric charge in the sensor caused by the mechanical stress on the sensor; and
    wherein the disposing step comprises:
    disposing a cardiac lead at a sensing location within the heart subject to mechanical stress due to cardiac contractions, the cardiac lead including an inner lead conductor that defines a stylet channel; and
    introducing a stylet into the stylet channel such that at least a portion of the stylet is disposed in the stylet channel at the sensing location, the stylet including a stylet conductor within an insulating sheath.

2. A method according to claim 1, wherein measuring a triboelectric charge in the sensor comprises measuring the triboelectric charge in the insulating sheath.

3. A method according to claim 2, wherein the measuring step comprises:
    measuring a voltage differential between the inner lead conductor and the stylet conductor to sense the triboelectric charge in the insulating sheath.

4. A method according to claim 1, wherein a modulation rate of the triboelectric charge in the sensor relates to a cardiac contraction rate.

5. A method according to claim 1, wherein the magnitude of the amplitude of the measured triboelectric charge relates to the strength of the mechanical contractions.

* * * * *